United States Patent
Kajiura

(10) Patent No.: US 8,177,337 B2
(45) Date of Patent: May 15, 2012

(54) FLOW PATH UNIT, INSPECTION APPARATUS, AND INSPECTION METHOD

(75) Inventor: Morimasa Kajiura, Ichinomiya (JP)

(73) Assignee: Brother Kogyo Kabushiki Kaisha, Nagoya-shi, Aichi-ken (JP)

( * ) Notice: Subject to any disclaimer, the term of this patent is extended or adjusted under 35 U.S.C. 154(b) by 546 days.

(21) Appl. No.: 12/168,746

(22) Filed: Jul. 7, 2008

(65) Prior Publication Data

US 2009/0009765 A1    Jan. 8, 2009

(30) Foreign Application Priority Data

Jul. 6, 2007    (JP) ................. 2007-178191

(51) Int. Cl.
*B41J 2/045* (2006.01)
(52) U.S. Cl. .......................... 347/71; 347/68
(58) Field of Classification Search .............. 347/68–72, 347/19, 65; 29/890.1; 250/559.08
See application file for complete search history.

(56) References Cited

U.S. PATENT DOCUMENTS

| | | | |
|---|---|---|---|
| 7,251,883 | B2 | 8/2007 | Nakamura et al. |
| 2002/0042994 | A1* | 4/2002 | Ito et al. ............ 29/890.1 |
| 2005/0195249 | A1* | 9/2005 | Nakamura et al. ........ 347/71 |
| 2006/0218781 | A1 | 10/2006 | Nakamura et al. |

FOREIGN PATENT DOCUMENTS

| | | | |
|---|---|---|---|
| JP | 2000-141667 A | | 5/2000 |
| JP | 2001-030487 A | | 2/2001 |
| JP | 2002-036568 A | | 2/2002 |
| JP | 2004128224 A | | 4/2004 |
| JP | 2005-246841 | * | 9/2005 |
| JP | 2005-246841 A | | 9/2005 |
| JP | 2006-231796 A | | 9/2006 |
| JP | 2007-130788 A | | 5/2007 |

OTHER PUBLICATIONS

Japan Patent Office, Office Action for Japanese Patent Application No. 2007-178191 (counterpart to above-captioned patent application), issued Dec. 13, 2011.

* cited by examiner

*Primary Examiner* — Geoffrey Mruk
(74) *Attorney, Agent, or Firm* — Baker Botts L.L.P.

(57) ABSTRACT

A flow path unit of one aspect of the invention includes: a plurality of plates, each of the plurality of plates having a hole, the plurality of plates being laminated in a lamination direction with a predetermined positional relationship such that a flow path is formed by mutual communication of the holes provided at the plurality of plates. Each of the plurality of plates having a side surface, and a slit portion formed at the side surface, and the slit portions of the plurality of plates are connected to one another in the lamination direction of the plurality of plates. Each of widths of the slit portions of the plurality of plates is equal to or below an allowable error of a positional deviation of the plurality of plates so as to allow a formation of the flow path by the plurality of holes.

9 Claims, 4 Drawing Sheets

FLOW PATH UNIT, INSPECTION APPARATUS, AND INSPECTION METHOD

CROSS-REFERENCE TO RELATED APPLICATIONS

This application is based upon and claims the benefit of priority from Japanese Patent Application No. 2007-178191, filed on Jul. 6, 2007, the entire contents of which are incorporated herein by reference.

TECHNICAL FIELD

The present invention relates to of a flow path unit in which flow path are formed by laminating a plurality of plates, and an inspection apparatus and an inspection method which inspect the positional deviation of a plurality of plates laminated to form the flow path unit.

BACKGROUND

Generally, a flow path unit used for an ink-jet head of a printer is formed by laminating a plurality of plates having holes. The holes formed at the plurality of plates are laminated and communicate with one another, thereby forming ink flow paths through which ink flows. The ink which flows through the ink flow paths are discharged from nozzle holes formed at a lowermost plate. In this case, if the plurality of plates are not laminated precisely, variations will occur in the volume or flow path resistance of flow paths to be formed, and the ink discharge performance from the nozzle holes will be disrupted.

Thus, in order to align two plates, JP-A-2004-128224 discloses a method for inspecting a positional deviation. The method disclosed in JP-A-2004-128224 includes: holding a plate as a first electronic component on a receiving table; holding a plate as a second electronic component to a bottom surface of a position adjusting mechanism which is located above the first electronic component; and inspecting the positional deviation between the first electronic component and the second electronic component by a camera. The first electronic component has alignment holes passing therethrough in its thickness direction. The receiving table has see-through holes formed at positions corresponding to the alignment holes. Alignment marks smaller than the alignment holes are formed at a position corresponding to the alignment hole on the surface of the second electronic component which faces the first electronic component. Moreover, a dry film resist which serves as an adhesive is formed on the surface of the second electronic component which faces the first electronic component. The dry film resist has see-through holes at positions corresponding to the alignment marks.

As the method of inspecting the positional deviation described in JP-A-2004-128224, it is necessary to arrange the camera under the receiving table to correspond to the alignment holes to hold the alignment holes and the alignment marks within a focal depth, and then the camera picks up an image upward. In this state, the deviation between the center of the alignment hole and the center of the alignment mark is inspected.

However, in the positional deviation inspection method described in JP-A-2004-128224, as the number of plates laminated increases, the distance between the lowermost plate of the receiving table and the plate held by the position adjusting mechanism which is laminated above the lowermost plate may increase. Therefore, it is difficult to hold all the plates within the focal depth. Then, whenever a positional deviation is inspected, the camera should be focused on the lowermost plate or focused on the plate held by the position adjusting mechanism, and therefore, inspection efficiency degrades.

SUMMARY

One aspect of the invention has an object of to provide a flow path unit, an inspection apparatus, and an inspection method which improve inspection efficiency.

According to a first aspect of the invention, there is provided a flow path unit comprising: a plurality of plates, each of the plurality of plates having a hole, the plurality of plates being laminated in a lamination direction with a predetermined positional relationship such that a flow path is formed by mutual communication of the holes provided at the plurality of plates, wherein each of the plurality of plates having a side surface, and a slit portion formed at the side surface, and the slit portions of the plurality of plates are connected to one another in the lamination direction of the plurality of plates, and wherein each of widths of the slit portions of the plurality of plates is equal to or below an allowable error of a positional deviation of the plurality of plates so as to allow a formation of the flow path by the plurality of holes.

According to a second aspect of the invention, there is provided an inspection apparatus configured to inspect a positional deviation of a laminated plurality of plates with respect to a direction orthogonal to a lamination direction of the plates, the plurality of plates each having a hole and a slit portion that is formed at a side surface, the plurality of plates being laminated with a predetermined positional relationship to form a flow path unit such that a flow path is formed by mutual communication of the holes and the slit portions are connected to one another, the inspection apparatus comprising: a supporting base configured to support the laminated plurality of plates; and a camera configured to pick up an image of the slit portion formed at each of the side surface of the plurality of plates supported by the supporting base from the direction orthogonal to the side surfaces.

According to a third aspect of the invention, there is provided an inspection method for inspecting a positional deviation of a laminated plurality of plates with respect to a direction orthogonal to a lamination direction of the plates, the plurality of plates each having a hole and a slit portion that is formed at a side surface, the plurality of plates being laminated with a predetermined positional relationship to form a flow path unit such that a flow path is formed by mutual communication of the holes and the slit portions are connected to one another, the inspection method comprising: placing the laminated plurality of plates on a supporting base, and picking up an image of the slit portions formed at the plurality of plates placed on the supporting base from the direction orthogonal to the side surfaces.

DESCRIPTION

Figure 1:
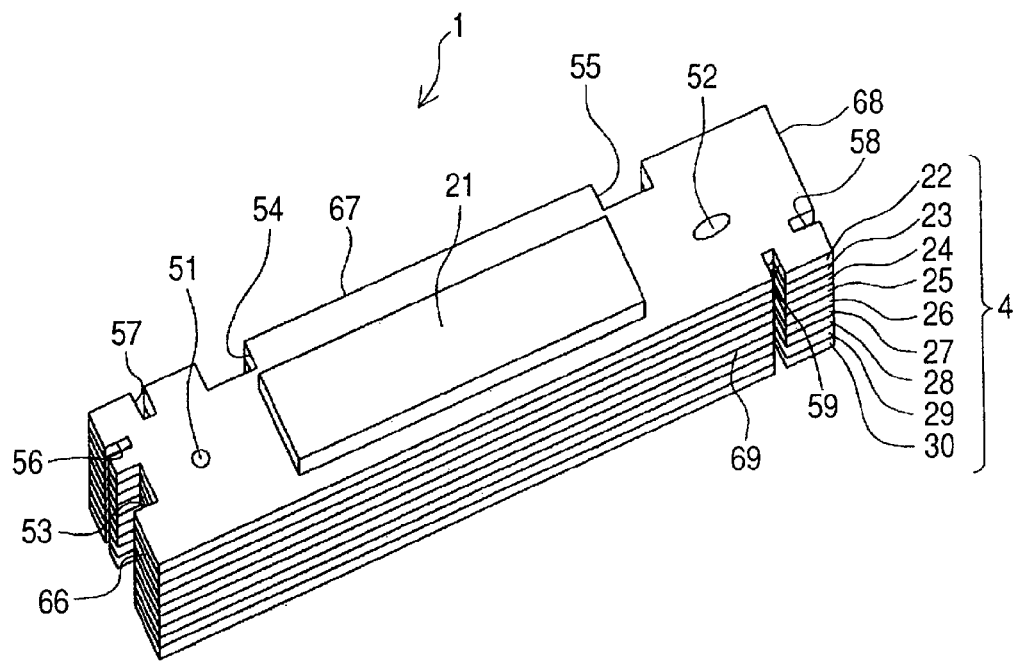
FIG. 1 is a schematic perspective view of an ink-jet head according to one embodiment of the invention.
Figure 2:
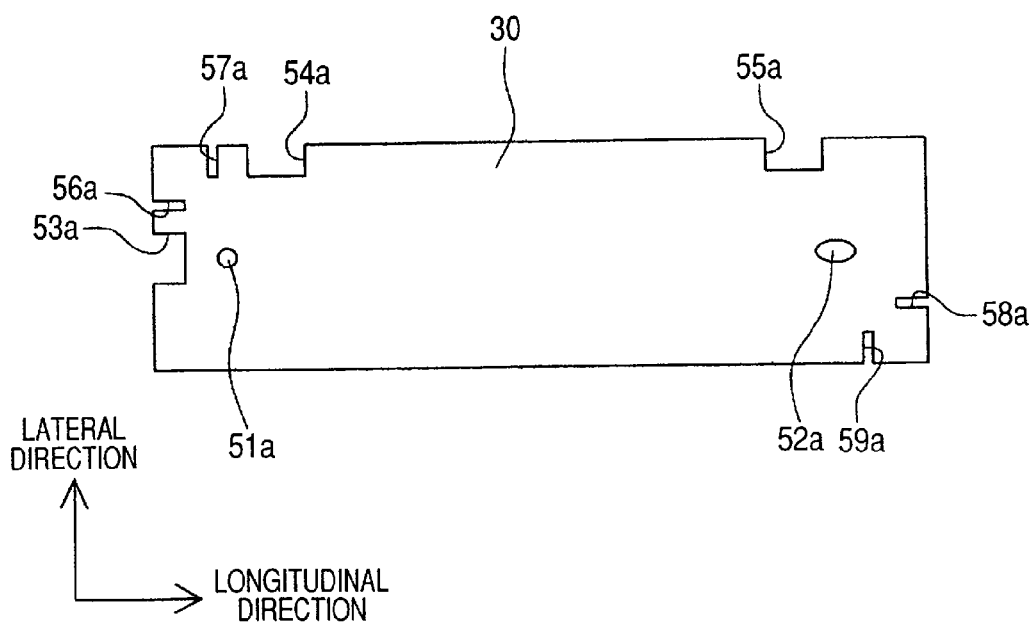
FIG. 2 is a schematic plan view of a flow path unit.
Figure 3:
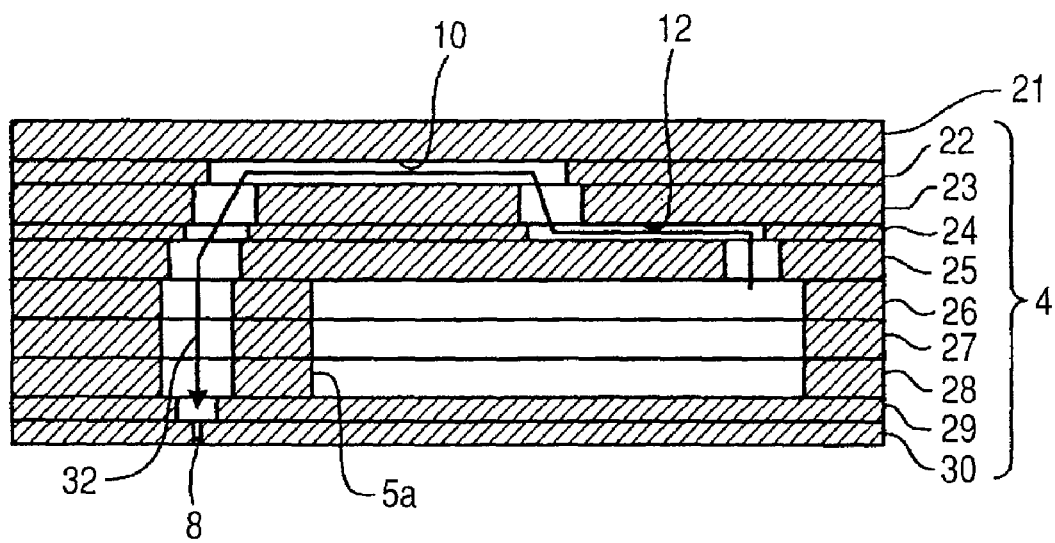
FIG. 3 is a partially sectional view of the ink-jet head.

Hereinafter, a preferred embodiment of the invention will be described with reference to the drawings. An embodiment to be described below is one in which the invention is applied to an ink-jet head which discharges ink. FIG. 1 is a schematic perspective view of an ink-jet head according to one embodiment of the invention. FIG. 2 is a schematic plan view of a nozzle plate. FIG. 3 is a partially sectional view of the ink-jet head.

As shown in FIGS. 1 to 3, the ink-jet head 1 includes a flow path unit 4 having rectangular shape which is long in one direction, and an actuator unit 21 fixed to the top surface of the flow path unit 4. The flow path unit 4 has a laminated structure in which a cavity plate 22, a base plate 23, an aperture plate 24, a supply plate 25, manifold plates 26, 27, and 28, a cover plate 29, and a nozzle plate 30 are laminated from the top.

As shown in FIG. 3, the cavity plate 22 is a metal plate having a number of holes to be pressure chambers 10. The base plate 23 is a metal plate having a number of communication holes for allowing each of the pressure chambers 10 and respective apertures 12 communicate with each other, and a number of communication holes for allowing the pressure chamber 10 and respective nozzle holes 8 to communicate with each other. The aperture plate 24 is a metal plate having holes to be the respective apertures 12, and a number of communication holes for allowing each of the pressure chambers 10 and the respective nozzle holes 8 to communicate with each other. The supply plate 25 is a metal plate having a number of communication holes for allowing each of the apertures 12 and an auxiliary manifold flow path 5a to communicate with each other, and a number of communication holes for allowing each of the pressure chambers 10 and the respective nozzle holes 8 to communicate with each other. The manifold plates 26, 27, and 28 are metal plates each having a number of communication holes for allowing a hole to be the auxiliary manifold flow path 5a, and each of the pressure chambers 10 and the respective nozzle holes 8 to communicate with each other. The cover plate 29 is a metal plate having a number of communication holes for allowing each of the pressure chambers 10 and the respective nozzle holes 8 to communicate with each other. The nozzle plate 30 is a metal plate having the nozzle holes 8 whose diameter is smaller than the holes formed at the other metal plates 22 to 29.

The nine metal plates 22 to 30 are mutually aligned and laminated such that individual ink flow paths 32 are formed inside the laminated structure. The ink, which has flowed in from an ink supply port (not shown), flows into each of the individual ink flow paths 32 via the auxiliary manifold flow path 5a. In the individual ink flow path 32, the ink which has flowed in from the auxiliary manifold flow path 5a reaches the nozzle hole 8 via the pressure chamber 10.

As shown in FIGS. 1 and 2, the flow path unit 4 has a reference hole 51 (an example of a reference point), a long hole 52, three cutouts 53 to 55, and four slits 56 to 59. The reference hole 51, the long hole 52, the three cutouts 53 to 55, and the four slits 56 to 59 are formed by laminating the metal plates 22 to 30. Therefore, only the nozzle plate 30 will be described and the description regarding the remaining plates 22 to 29 will be omitted.

A reference hole 51a is formed at the middle of the nozzle plate 30 with respect to its lateral direction (short side direction; direction orthogonal to the longitudinal direction for an in-plane direction) at one longitudinal end portion (left end portion in FIG. 2) thereof. The reference hole 51a has a circular planar shape and is formed so as to pass through the nozzle plate 30 in its thickness direction. As the respective metal plates 22 to 30 are laminated such that the centers of the reference holes formed in the respective metal plates 22 to 30 are arranged in the same position in the lamination direction, the reference hole 51 which passes through the flow path unit 4 in its lamination direction is formed.

A long hole 52a is formed in the middle of the nozzle plate 30 in the lateral direction at the other longitudinal end portion (right end portion in FIG. 2) thereof. The long hole 52a has an elliptical planar shape along the longitudinal direction, and is formed so as to pass through the nozzle plate 30 in its thickness direction. As the respective metal plates 22 to 30 are laminated such that the centers of the long holes formed in the respective metal plates 22 to 30 are arranged in the same position in the lamination direction, the reference hole 52 is formed to pass through the flow path unit 4 in its lamination direction.

A cutout 53a which is cut out in a rectangular shape is formed in the middle of the nozzle plate 30 at one longitudinal end portion on the side where the longitudinal reference hole 51a is formed. Moreover, cutouts 54a and 55a which are cut out in a rectangular shape similarly to the cutout 53a are formed in the vicinity of both ends of the nozzle plate 30 at one lateral end (upper end in FIG. 2) thereof. As the respective metal plates 22 to 30 are laminated such that the centers of the cutouts formed in the respective metal plates 22 to 30 are arranged in the same position in the lamination direction, the reference holes 53 to 55 which pass through the flow path unit 4 in the lamination direction are formed. In addition, since the three cutouts 53 to 55 are formed by machining, surface accuracy is high. Although described below in detail, the three cutouts 53 to 55 are provided to correct the positional deviation of the metal plates 22 to 30 which are laminated.

A slit 56a which is cut out in a rectangular shape is formed on the side of one end portion of the nozzle plate 30 where the cutout 54a is formed at one end portion where the cutout 53a is formed. Moreover, a slit 57a which is cut out in a rectangular shape is formed on the side of one end portion of the nozzle plate 30 where the cutout 53a is formed at one end portion thereof where the cutout 54a is formed. Further, the slits 58a and 59a which are cut out in a rectangular shape are formed at the positions of the nozzle plate 30 which are point-symmetrical with the slits 56a and 57a about the center of the nozzle plate 30. As the respective metal plates 22 to 30 are laminated such that the centers of the slits are arranged in the same position in the lamination direction, the slits 56 to 59 which pass through the flow path unit 4 in its lamination direction is formed.

Figure 4:
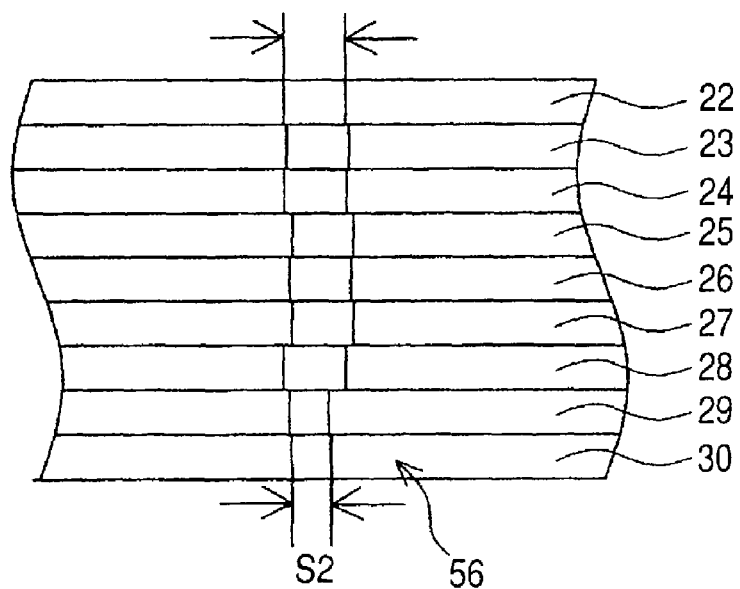
FIG. 4 is an enlarged plan view of slits formed in the flow path unit.

The opening width of each of the slits 56 to 59, as shown in FIG. 4, is set to a width which is equal to or below the amount of deviation between metal plates in which the ink discharge characteristics between the individual ink flow paths 32 are below a predetermined value when the metal plates 22 to 30 are laminated. A maximum permissible difference of this positional deviation corresponds to a maximum amount of deviation to which deterioration of printing quality is not recognized, and becomes the opening width (for example, 50 μm: S1) of a slit corresponding to the maximum amount of deviation. Moreover, the opening width S2 of the slits formed in the cover plate 29 and the nozzle plate 30 is made smaller than the opening width S1 of the slits formed in the other metal plates 22 to 28. This is because that the nozzle holes 8 formed in the nozzle plate 30 have a smaller diameter than the holes formed in the metal plates 22 to 29. By making the opening width of the slits formed in the nozzle plate 30 and the cover plate 29 laminated adjacent to the nozzle plate 30 narrower than the opening width of the slits formed in the other metal plates 22 to 28 as described above, it becomes possible to inspect a positional deviation between the nozzle plate 30 and the cover plate 29 laminated adjacent to the nozzle plate 30 with high precision.

As shown in FIG. 3, the actuator unit 21 configures a number of actuators which give discharge energy to the ink within each pressure chamber 10. By supplying a predetermined voltage pulse from a driving driver (not shown) to the actuator unit 21, a pressure wave (discharge energy) is created in the ink within the pressure chamber 10, and ink droplets are discharged from the nozzle hole 8 communicating with the pressure chamber 10.

According to the flow path unit 4 described above, the slits 56 to 59 have an opening width which is equal to or below an allowable error in which the individual ink flow paths 32 provided with ink discharge characteristics can be formed, and are formed at side surfaces of a laminated structure. Thus, it becomes possible to easily inspect the continuity of the slits 56 to 59 in the lamination direction with a camera. That is, it becomes possible to inspect the whole continuity of the respective slits 56 to 59 only by focusing the camera on the side surfaces of the metal plates 22 to 30 (laminated structure) once. For this reason, the inspection efficiency of the positional deviation of each of the metal plates 22 to 30 improves.

Further, since the slits 56 to 59 are respectively formed in the longitudinal direction of the metal plates 22 to 30 and in the lateral direction orthogonal thereto, it becomes possible to inspect the positional deviation of the metal plates 22 to 30 in the longitudinal direction and in the lateral direction orthogonal thereto. Therefore, the inspection accuracy becomes higher. As a result, assembling accuracy improves.

Moreover, as the slit 58 is formed at one end portion in the lateral direction apart from the reference hole 51, it becomes possible to make an inspection even in a spot where the amount of positional deviation of the metal plates 22 to 30 is relatively large. Therefore, the inspection accuracy becomes higher. As a result, the assembling accuracy further improves.

In addition, since the slits 58 and 59 are disposed point-symmetrically with the slits 56 and 57 about the center of each of the metal plates 22 to 30, it becomes easy to design the positions of the slits 56 to 59 in each of the metal plates 22 to 30.

Further, since the cutouts 53 to 55 are formed in the long and short sides of each of the metal plates 22 to 30, it becomes possible to correct the positional deviation of the metal plates 22 to 30 in the longitudinal direction and in the lateral direction orthogonal thereto.

Moreover, as the opening width of the cutouts 53 to 55 is larger than the opening width of the slits 56 to 59, and the cutouts 53 to 55 are pressed against a correction pin as described later, it becomes possible to correct the positional deviation of each of the metal plates 22 to 30.

Figure 5:
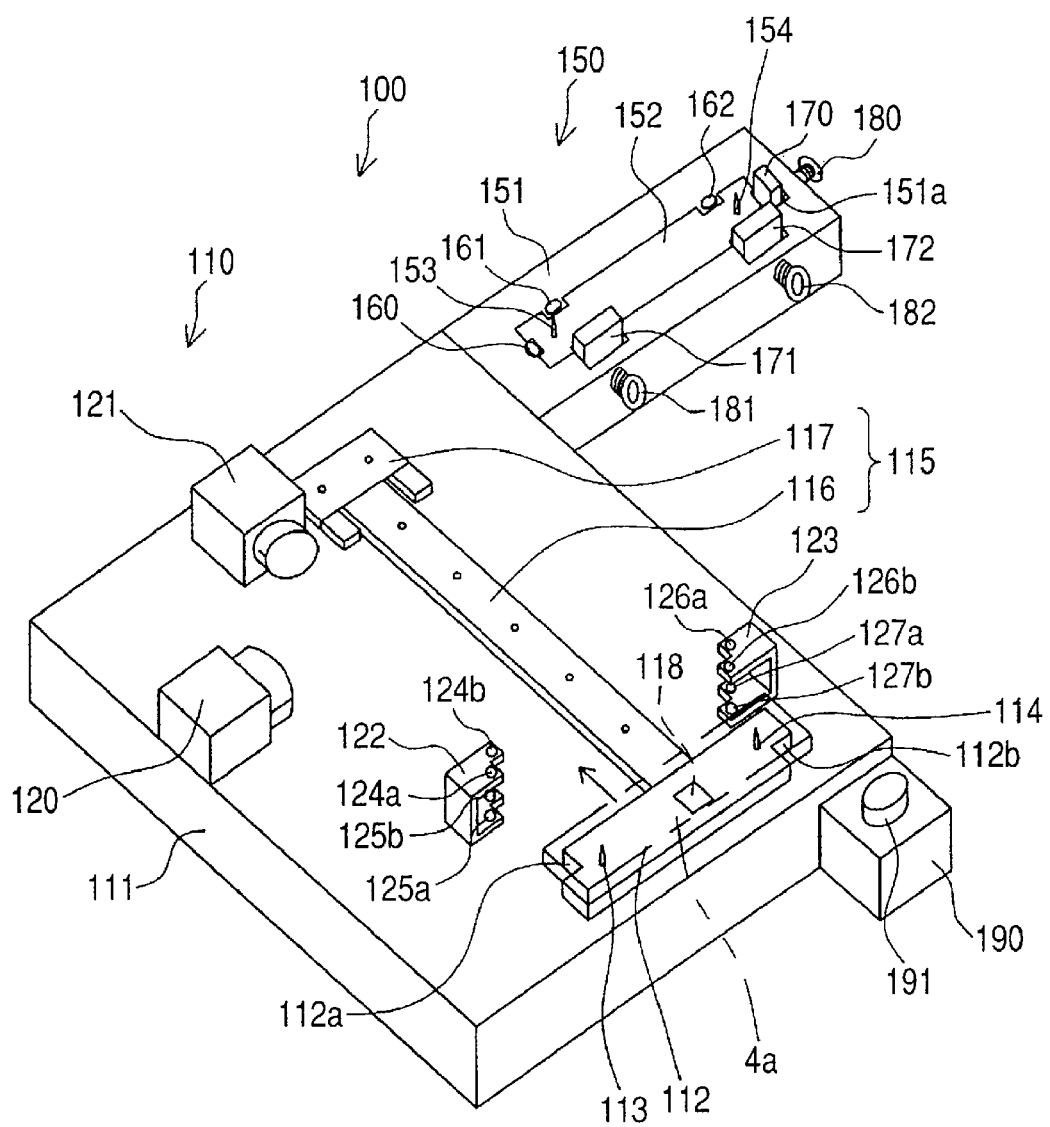
FIG. 5 is a schematic perspective view of an inspection apparatus.

Next, an inspection apparatus which inspects and corrects the positional deviation of the laminated metal plates 22 to 30 which constitute the flow path unit 4 will be described with reference to FIG. 5. FIG. 5 is a schematic perspective view of the inspection apparatus.

As shown in FIG. 5, the inspection apparatus 100 has an inspection section 110 which inspects a positional deviation in a direction (the long-side direction and short-side direction of the metal plates 22 to 30) orthogonal to the lamination direction of the metal plates 22 to 30, a correction unit 150 which corrects the positional deviation in the direction orthogonal to the lamination direction of the metal plates 22 to 30, and an operation unit 190 which operates the inspection section 110. The inspection apparatus 100 operates the operation unit 190 to inspect the positional deviation of the metal plates 22 to 30 by the inspection section 110, and if there is a positional deviation, correct the positional deviation by the correction unit 150.

The inspection section 110 has an inspection table 111 of a rectangular parallelepiped shape, a supporting base 112 configured to support the flow path unit 4, a conveyor mechanism 115 configured to convey the supporting base 112 in one direction, cameras 120 and 121 configured to pick up images of the four slits 56 to 59 formed in the flow path unit 4, and laser inspection sections 122 and 123 configured to radiate and receive laser beams.

The supporting base 112 has a rectangular shape, and has a size which is substantially the same size as the metal plates 22 to 30. The supporting base 112 has a cutout 112a which overlaps the slits 56 and 57 in the lamination direction and a cutout 112b which overlaps the slits 58 and 59 in the lamination direction, when the flow path unit 4 is placed thereon. The supporting base 112 has tapered locating pins 113 and 114 which protrude upward. The locating pins 113 and 114 are fixed at positions of the supporting base 112 such that the locating pins 113 and 114 are respectively inserted into the reference hole 51 and the long hole 52 when the flow path unit 4 is placed on the supporting base 112. Each of the diameters of the locating pins 113 and 114 is smaller than the diameter of the reference hole 51 and the long hole 52.

The conveyor mechanism 115 includes a conveyor rail 116 extending in one direction on the top surface of the inspection table 111, and a drive mechanism 117 provided at one end of the conveyor rail 116. A rotating mechanism 118 is supported by the conveyor rail 116. The rotating mechanism 118 is configured such that its bottom surface portion is slidable along the conveyor rail 116 and its top surface portion is rotatable with respect to the conveyor rail 116. The center of the bottom surface of the supporting base 112 and the top surface portion of the rotating mechanism 118 are fixed. The drive mechanism 117 is configured to move the rotating mechanism 118 along the conveyor rail 116 by driving a driving motor (not shown). Consequently, the supporting base 112 moves along the conveyor rail 116. Further, the drive mechanism 117 is configured to drive the rotary motor (not shown) to rotate the rotating mechanism 118, thereby rotating the supporting base 112 about its center by 180 degrees.

The camera 120 is provided toward an image pick-up direction in a direction orthogonal to an extending direction of the conveyor rail 116 at one end portion of the top surface of the inspection table 111 in the direction orthogonal to the extending direction of the conveyor rail 116. The camera 120 is configured to pick up an image of the slit 56 from the direction orthogonal to a side surface 66 in which the slit 56 of the flow path unit 4 is formed, when the flow path unit 4 supported by the supporting base 112 has moved along the conveyor rail 116. Further, the camera 120 is configured to pick up an image of the slit 58 from the direction orthogonal to a side surface 68 in which the slit 58 of the flow path unit 4 is formed, as the flow path unit 4 has rotated by 180 degrees by the rotation of the rotating mechanism 118.

The camera 121 is provided toward an image pick-up direction in the extending direction of the conveyor rail 116 on the left of the driving mechanism 117 on the top surface of the inspection table 111. The camera 121 is configured to pick up an image of the slit 57 from the direction orthogonal to a side surface 67 in which the slit 57 of the flow path unit 4 is formed, when the flow path unit 4 supported by the supporting base 112 has moved along the conveyor rail 116. Further, the camera 121 is configured to pick up an image of the slit 59 from the direction orthogonal to a side surface 69 in which the slit 59 of the flow path unit 4 is formed, as the flow path unit 4 has rotated by 180 degrees by the rotation of the rotating mechanism 118.

The laser inspection section 122 is provided on the top surface of the inspection table 111, and includes laser beam radiating units 124a and 124b configured to radiate laser beams, and laser beam receiving units 125a and 125b configured to receive the laser beams emitted from the laser beam radiating units 124a and 124b. The laser beam radiating units 124a and 124b and the laser beam receiving units 125a and 125b are provided at positions where the laser beams emitted from the laser beam radiating units 124a and 124b can be received by the laser beam receiving units 125a and 125b via the slits 56 and 57 when the flow path unit 4 supported by the supporting base 112 has moved along the conveyor rail 116.

The laser inspection section 123 is provided on the top surface of the inspection table 111, and includes laser beam radiating units 126a and 126b configured to radiate laser beams, and laser beam receiving units 127a and 127b which receive the laser beams emitted from the laser beam radiating units 126a and 126b. The laser beam radiating units 126a and 126b and the laser beam receiving units 127a and 127b are provided at positions where the laser beams emitted from the laser beam radiating units 126a and 126b can be received by the laser beam receiving units 127a and 127b via the slits 58 and 59 when the flow path unit 4 supported by the supporting base 112 has moved along the conveyor rail 116.

The correction unit 150 includes: a correction table 151 of a rectangular parallelepiped shape; a placing base 152 configured to place thereon the flow path unit 4 which has positional deviations of plates; and tapered locating pins 153 and 154 which protrude upward. The locating pins 153 and 154 are fixed on the placing base 152 such that the locating pins 153 and 154 are respectively inserted into the reference hole 51 and the long hole 52 when the flow path unit 4 is placed on the placing base 152. The diameters of the locating pins 153 and 154 are smaller than the diameters of the locating pins 113 and 114.

The correction unit 150 includes correction pins 160 to 162 (first abutting portion, second abutting portion) which can abut on the cutouts 53 to 55 when the flow path unit 4 is placed on the placing base 152; pushing blocks 170 to 172 provided at positions which face the correction pins 160 to 162 across the placing base 152; and pushing screws 180 to 182 which can move the pushing blocks 170 to 172 toward the correction pins 160 to 162.

The pushing block 170 is disposed within a hole 151a formed in the correction table 151, and protrudes from the top surface of the correction table 151. A side surface the pushing block 170 abuts on the tip of the pushing screw 180 which is screwed in from a side surface of the correction table 151. By fastening the pushing screw 180, the pushing block moves toward the correction pin 160, and abuts on the flow path unit 4 placed on the placing base 152. Moreover, if the pushing screw 180 is fastened, the pushing block 170 moves toward the correction pin 160 in the state of abutting the flow path unit 4, and makes the flow path unit 4 abut on the correction pin 160, thereby eliminating the positional deviation of the metal plates 22 to 30 in the longitudinal direction.

The pushing blocks 171 and 172 have the same configuration as the pushing block 170 and make the flow path unit 4 placed on the placing base 152 abut on the correction pins 161 and 162 by fastening the pushing screws 181 and 182 screwed in from side surfaces of the correction table 151, thereby eliminating the positional deviation of the metal plates 22 to 30 in the lateral direction.

The operation unit 190 has an operation button 191. By operating the operation button 191, inspection of the positional deviation of the flow path unit 4 is started.

According to the inspection apparatus 100 described above, the laser inspection sections 122 and 123 are provided. Thus, by whether or not a laser beam can pass through a series of the plural slits, it is possible to rapidly determine whether or not an amount of deviation is within an allowable range. Once the flow path unit 4 traverses the laser inspection sections 122 and 123, this determination is allowed. Thus, the inspection efficiency of a positional deviation is high.

Further, the cameras 120 and 121 are provided. Thus, by focusing the cameras once to pick up images, it is possible to inspect all the slits 56 to 59 simultaneously. Thereby, it is possible to specify the degree of the deviation of any of the respective metal plates 22 to 30. Thereby, the correction operation by the correction pins 160 to 162 can be reliably performed, which leads to the improvement of the assembling process.

The correction pins 160 to 162 are provided. Thus, by pressing the cutouts 53 to 55 of the metal plates 22 to 30 against the correction pins 160 to 162, it is possible to correct the positional deviation of the metal plates 22 to 30 in the longitudinal direction and in the lateral direction. At this time, the positional deviation is corrected by pressing not the side surfaces of the metal plates 22 to 30 but the cutouts 53 to 55 against the correction pins 160 to 162. Therefore, it is not necessary to form all the side surfaces of the metal plates 22 to 30 precisely but it is only necessary to form only the cutouts 53 to 55 precisely.

Figure 6:
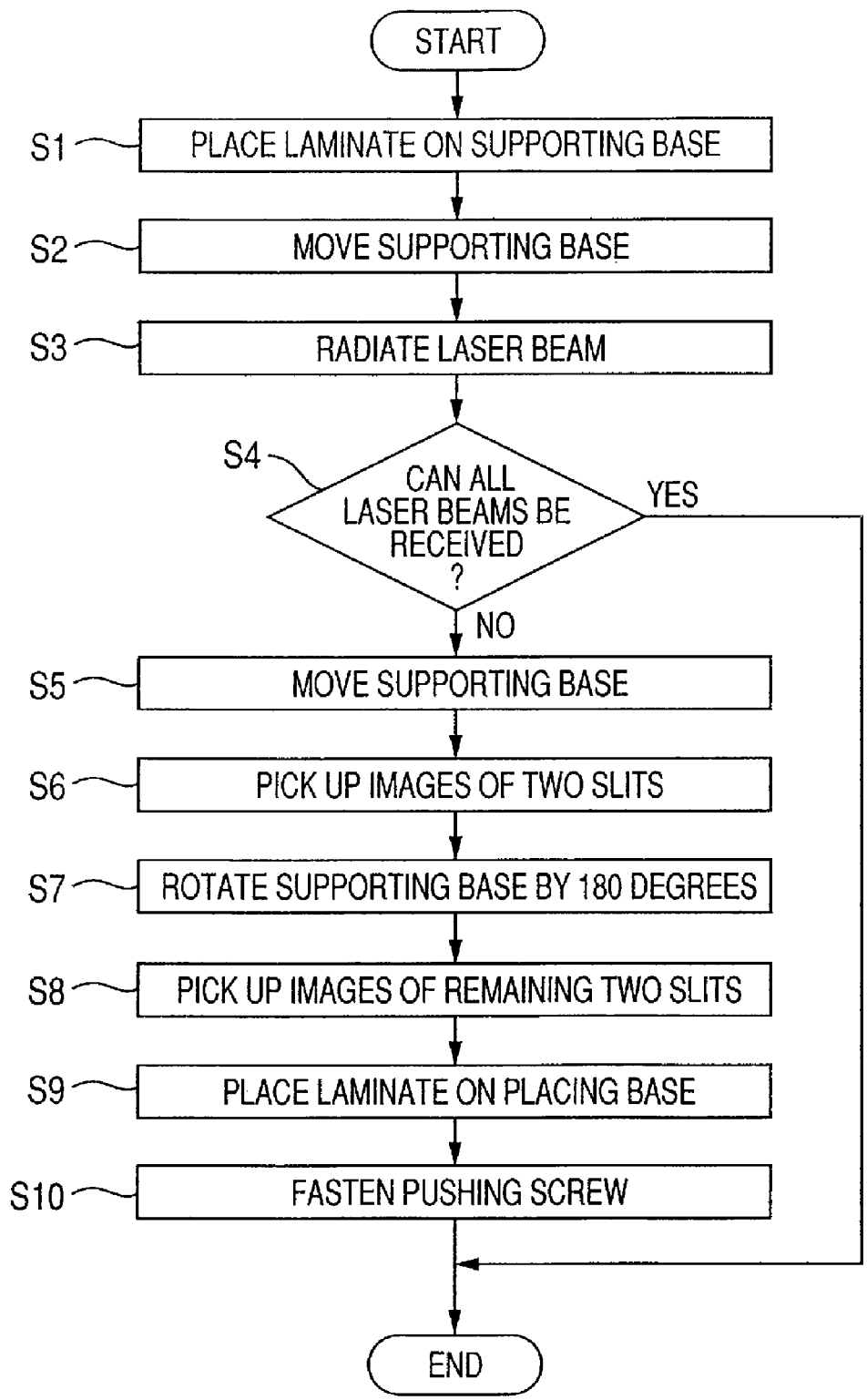
FIG. 6 is a flow chart of a series of operations which inspects a positional deviation.

Subsequently, a series of operations which inspects the positional deviation in the direction orthogonal to the lamination direction of the flow path unit 4 will be described with reference to FIG. 6. FIG. 6 is a flow chart of a series of operations to inspect a positional deviation.

The respective metal plates 22 to 30 are laminated via thermosetting resin. When a positional deviation is inspected, the inspection is performed in the state of a laminate 4a which is not cured, i.e., before being thermally cured. First, the laminate 4a which is configured by laminating the metal plates 22 to 30 is placed on the supporting base 112 of the inspection section 110 (S1: placing step). Next, the operation button 191 of the operation unit 190 is pushed to drive the driving motor of the driving mechanism 117, thereby moving the supporting base 112 along the conveyor rail 116 together with the rotating mechanism 118. Then, when the slits 56 to 59 formed in the laminate 4a are located on imaginary straight lines starting from the laser beam radiating units 124a, 124b, 126a, and 126b to the laser beam receiving units 125a, 125b, 127a and 127b, respectively, the driving motor of the driving mechanism 117 is stopped, and thereby, the movement of the supporting base 112 is stopped (S2).

In this state, a laser beam is radiated to each of the laser beam receiving units 125a and 125b and 127a and 127b from each of the laser beam radiating units 124a, 124b, 126a, and 126b, that is, in the lamination direction of the respective metal plates 22 to 30 (S3), and it is determined whether or not laser beams can be received by all the laser beam receiving units 125a, 125b, 127a, and 127b (S4: radiating step). If the laser beams can be received by all the laser beam receiving units 125a, 125b, 127a, and 127b (S4: Yes), it is determined that the flow path unit 4 does not deviate in position, and then, the laminate 4a is burned and cured, thereby forming the flow path unit 4.

If any laser beam cannot be received by at least one of the laser beam receiving units 125a, 125b, 127a, and 127b (S4: No), at least one plate of the metal plates 22 to 30 deviates in the direction orthogonal to the lamination direction and shields the laser beam. Therefore, it is determined that the laminate 4a deviates in position. Then, the driving motor of the driving mechanism 117 is driven, thereby further moving the supporting base 112 along the conveyor rail 116 together with the rotating mechanism 118. Then, when the slits 56 and 57 are located within the image pick-up ranges of the cameras 120 and 121, the driving motor of the drive mechanism 117 is stopped, and thereby, the movement of the supporting base 112 is stopped (S5).

Then, the images of the slits 56 and 57 are picked up by the cameras 120 and 121, and it is determined the degree of the positional deviation of any plate based on a series of the slits 56 and 57 (S6).

Subsequently, the rotary motor of the drive mechanism 117 is driven to rotate the rotating mechanism 118 by 180 degrees, thereby rotating the supporting base 112 by 180 degrees about its center (S7). Then, the images of the slits 58 and 59 are picked up by the cameras 120 and 121, and it is determined the degree of the positional deviation of any plate based on a series of the slits 58 and 59 (S8: image pick-up step). By picking up the image of each of the slits 56 to 59 from the direction orthogonal to all the side surfaces 66 to 69 by the cameras 120 and 121, tendencies such as of the site, direction, and amount of a positional deviation can be evaluated.

Next, the laminate 4a is placed on the placing base 152 of the correction unit 150 (S9). Then, by suitably fastening the pushing screws 180 to 182, the positional deviation of the laminate 4a is eliminated (S10). At this time, it becomes possible to adjust the fastening amount of the pushing screws 180 to 182, i.e., the travel distance of the pushing blocks 170 to 172, on the basis of the direction and degree of the positional deviation of the laminate 4a which are evaluated in S6 and S8. Thus, a positional deviation can be rapidly and properly corrected, and the correction and inspection time of the positional deviation can be shortened.

According to the inspection method described above, the laser inspection sections 122 and 122 are provided. Thus, by whether or not a laser beam can pass through a series of the plural slits, it is possible to rapidly determine whether or not an amount of deviation is within an allowable error range. Once the flow path unit 4 traverses the laser inspection sections 122 and 123, this determination is allowed. Thus, the inspection efficiency of a positional deviation is high.

Further, the cameras 120 and 121 are provided. Thus, by focusing the cameras once to pick up images, it is possible to inspect all the slits 56 to 59 simultaneously. Thereby, it is possible to specify the deviation of any of the respective metal plates 22 to 30. Thereby, the correction operation by the correction pins 160 to 162 can be reliably performed. Moreover, the assembling process can be improved from the evaluation results of tendencies, such as the site, direction, and amount of a positional deviation.

Although the embodiment of the invention has been described hitherto, the invention is not limited to the above-mentioned embodiment, and can be modified, and various changes thereof can be made. For example, in the above-mentioned embodiment, the correction unit 150 corrects the positional deviation of the flow path unit 4. However, the correction unit 150 may not be provided if only the positional deviation of the flow path unit 4 is detected. At this time, the slits 53 to 55 may not be formed in the flow path unit 4.

Further, in this embodiment, the slits 56 to 59 are formed at all the sides of the flow path unit 4. However, in a case where tendencies, such as the direction and amount of a positional deviation of the flow path unit 4, can be known in advance, slits may be provided only in places where a positional deviation occurs easily. That is, slits can be formed in arbitrary places.

Moreover, in this embodiment, the flow path unit 4 is provided with the reference hole 31 and the long hole 32. However, in a case where guides are provided at the side surfaces of the flow path unit 4, it is not necessary to provide the flow path unit 4 with the reference hole 31 and the long hole 32. In this case, the locating pins 113 and 114 may not be provided in the supporting base 112.

In addition, in this embodiment, the opening width of the slits formed in the cover plate 29 and the nozzle plate 30 is made smaller than the opening width of the slits formed in the other metal plates 22 to 28. However, as long as it is not necessary to inspect the positional deviation of the cover plate 28 and the nozzle plate 30 with high precision, the opening width of the slits formed in the cover plate 29 and the nozzle plate 30 may be the same as that of the opening width of the slits formed in the other metal plates 22 to 28. Further, as long as it is desired that the positional deviation of all the metal plates 22 to 30 is inspected with high precision, the opening width of the slits formed in the metal plate 22 to 30 may be made small similarly to the slits formed in the cover plate 29 and the nozzle plate 30.

Further, from the viewpoint that the propagation characteristics of pressure waves induced by the flow path resistance from an outlet of the auxiliary manifold flow path 5a to the pressure chamber 10, or an actuator are made uniform, the opening width of the slits of the cavity plate 22, the base plate 23, and the aperture plate 24 may be made smaller than the other metal plates 25 to 28, irrespective of the opening width of the slits of the cover plate 29 and the nozzle plate 30. Thereby, refill characteristics of supplying ink to the pressure chamber after ink discharge, or the discharge precision of ink will be equalized.

Further, in this embodiment, the laser radiating step by the laser inspection sections 122 and 123 is provided. However, the laser inspection sections 122 and 123 may not be provided, and the laser radiating step may not be performed. In this case, the magnitude relation of a positional deviation to an allowable error may be determined by recognizing the image pick-up results of the cameras 120 and 121 in patterns.

Moreover, in this embodiment, the supporting base 112 is rotated by 180 degrees by the rotating mechanism 118, and then the images of the slits 58 and 59 are picked up from the direction orthogonal to the side surfaces 68 and 69 by the cameras 120 and 121. However, two cameras may be additionally provided, and the images of the slits 58 and 59 may be picked up from the direction orthogonal to the side surfaces 68 and 69 by these cameras. In this case, the rotating mechanism 118 may not be provided.

Further, the invention is not limited to the flow path unit of the ink-jet head like the above-mentioned embodiment, and can be applied to various flow path units if the flow path unit is a flow path unit which discharges liquid.

The flow channel unit of one embodiment of the invention is a flow path unit in which a plurality of plates in each of which a hole is formed are laminated in a predetermined positional relationship so that a flow path may be formed by mutual communication of the holes, side surfaces of each of the plates are formed with slits which are connected to one another in a lamination direction of the plurality of plates, and the opening width of the slits is below an allowable error of the positional deviation of the plurality of plates so as to allow the formation of the flow path by the plurality of holes.

According to the flow path unit of the embodiment of the invention, the slits having an opening width which is below an allowable error in which the flow paths can be formed are formed at side surfaces of each of the plates. Thus, it becomes possible to easily inspect the continuity of the slits in the lamination direction with a camera. That is, the slits are formed at side surfaces of the plurality of the plates which constitute the same plate. Thereby, it becomes possible to easily inspect the continuity of the plurality of slits only by focusing the camera once. For this reason, the inspection efficiency of the positional deviation of the plurality of plates can be improved.

The plurality of plates may have a rectangular shape which is long in one direction, and the slits are formed at long and short sides, respectively, of each of the plates. Thereby, it becomes possible to inspect the positional deviation of the plates in the longitudinal direction and in the lateral direction orthogonal thereto. Therefore, the inspection accuracy becomes higher.

Reference points which overlap one another in the lamination direction may be formed at one end of each of the plates in their lamination direction, and the slits may be formed at the other end of each of the plates. Thereby, it becomes possible to inspect the other end in which the positional deviation of the plates is relatively large as being separated from the reference point. Therefore, the inspection accuracy becomes higher.

The slits may be further formed at one end of each of the plates. Thereby, it becomes possible to inspect the positional deviation of the plates even at one end. Therefore, the inspection accuracy becomes higher.

The slits may be arranged point-symmetrically about the center of each of the plates. Thereby, the positions of the slits in each of the plates are easily designed.

Cutouts which are the same in positional relationship to the slits, and are connected to each other in the lamination direction may be formed at the side surfaces of each of the plates, and the opening width of the cutouts is larger than the opening width of the slits. Thereby, cutouts which are connected to each other are formed at side surfaces of each of the plurality of plates. Thus, as the cutouts are pressed against the abutting portion, it becomes possible to correct the positional deviation of the plates.

The plurality of plates may have a rectangular shape which is long in one direction, and the slits may be formed at long and short sides of each of the plates. Thereby, it becomes possible to inspect the positional deviation of the plates in the longitudinal direction and in the lateral direction orthogonal thereto.

The hole formed in one plate arranged on the outermost side of the plurality of plates may be a nozzle hole having a smaller diameter than the holes formed in the other plates than the one plate, and the slits formed in the plate in which the nozzle hole may be formed, and in the plate laminated adjacent thereto are narrower than those of the plates other than the two plates. Thereby, it becomes possible to inspect the positional deviation of the plate in which the nozzle hole is formed, and the plate laminated adjacent thereto.

The inspection apparatus of one embodiment of the invention is an inspection apparatus which inspects the positional deviation of a plurality of plates of a flow path unit in a direction orthogonal to a lamination direction of the plates, the plurality of plates each having a hole and slits formed at its side surfaces being laminated in a predetermined positional relationship so that a flow path may be formed by mutual communication of the holes and the slits are connected to one another. The inspection apparatus includes a supporting base which supports the flow path unit, and a camera which picks up an image of the slits formed in each of the plates which constitute the flow path unit supported by the supporting base from the direction orthogonal to the side surfaces.

According to the inspection apparatus of the one embodiment of the invention, it becomes possible to easily inspect the continuity of the plurality of slits only by focusing the camera once. For this reason, the inspection efficiency of the positional deviation of the plurality of plates which constitute the flow path unit improves. In addition, since it is possible to expect the degree of the deviation of any one of the plurality of plates, it is possible to determine whether or not the amount of deviation is within an allowable error range.

The inspection apparatus may further include a laser beam radiating unit which radiates a laser beam in the lamination direction, and a laser beam receiving unit which receives the laser beam radiated from the laser beam radiating unit via the slits. Thereby, it becomes possible to more easily inspect the continuity of the plurality of slits.

The plurality of plates may have a rectangular shape which is long in one direction, and the inspection apparatus further includes a first abutting portion which is arranged so as to be capable of abutting on one longitudinal side surface of each of the plurality of plates, and a second abutting portion which is arranged so as to be capable of abutting on one lateral side surface of each of the plurality of plates. Thereby, since the first and second abutting portions are provided, the positional deviation of the plates in the longitudinal direction and the lateral direction orthogonal thereto can be corrected by pressing the side surfaces of the plurality of plates against these abutting portions.

The inspection method of one embodiment is an inspection method which inspects the positional deviation of a plurality of plates of a flow path unit in a direction orthogonal to a lamination direction of the plates, the plurality of plates each having a hole and slits formed at its side surfaces being laminated in a predetermined positional relationship so that a flow path may be formed by mutual communication of the holes and the slits are connected to one another. The inspection method includes a placing step of placing the flow path unit on a supporting base, and an image pick-up step of picking up an image of the slits formed in each of the plates which constitute the flow path unit placed on the supporting base from the direction orthogonal to the side surfaces.

According to the inspection method of the embodiment of the invention, it becomes possible to easily inspect the continuity of the plurality of slits only by focusing the camera on the side surfaces of each of the plates once in the image pick-up step. For this reason, the inspection efficiency of the positional deviation of the plurality of plates which constitute the flow path unit improves. In addition, since it is possible to expect the degree of the deviation of any one of the plurality of plates, it is possible to determine whether or not the amount of deviation is within an allowable error range.

The inspection method may further include a laser beam radiating step of radiating a laser beam in the lamination direction of the plurality of plates within the slits after the placing step and before the image pick-up step. Thereby, it becomes possible to more easily inspect the continuity of the plurality of slits.

What is claimed is:

1. A flow path unit comprising:
   a plurality of plates, each of the plurality of plates having a hole, the plurality of plates being laminated in a lamination direction with a predetermined positional relationship such that a flow path is formed by mutual communication of the holes provided at the plurality of plates,
   wherein each of the plurality of plates having a side surface, and a slit portion formed at the side surface, and the slit portions of the plurality of plates are connected to one another in the lamination direction of the plurality of plates, and wherein each of widths of the slit portions of the plurality of plates is equal to or below an allowable error of a positional deviation of the plurality of plates so as to allow a formation of the flow path by the plurality of holes.

2. The flow path unit according to claim 1, wherein the plurality of plates have a rectangular shape which is long in one direction to have a long side and a short side, and wherein the slit portion of each of the plurality of plates comprises a first slit and a second slit formed at the long side and the short side, respectively.

3. The flow path unit according to claim 2, wherein a reference point which overlaps one another in the lamination direction is formed at a first end portion of each of the plates with respect to the one direction, and wherein the first and second slits are formed at a second end portion of each of the plates which is opposite to the first end portion with respect to the one direction.

4. The flow path unit according to claim 3, wherein the slit portion of the each of the plurality of plates further includes at least one of a third slit and a fourth slit formed at the first end portion.

5. The flow path unit according to claim 4, wherein the first and second slits and the third and fourth slits are respectively arranged point-symmetrically about the center of each of the plates.

6. The flow path unit according to claim 1, wherein a cutout portion is formed at the side surface of each of the plurality of plates, the cutout portions of the plurality of plates are connected to one another in the lamination direction, and width of the cutout portion is larger than the width of the slit portion.

7. The flow path unit according to claim 6, wherein the plurality of plates have a rectangular shape which is long in one direction to have a long side and a short side, and wherein the cutout portion of each of the plurality of plates comprises a first cutout and a second cutout formed at the long side and the short side, respectively.

8. The flow path unit according to claim 1, wherein the plurality of plates comprises: a first plate arranged at an outermost side of the plurality of plates in the lamination direction; a second plate arranged adjacent to the first plate in the lamination direction; and one or more other plates arranged on other side of the second plate from the first plate in the lamination direction, wherein the hole provided at the first plate includes a nozzle hole having a smaller diameter than the holes formed at the second plate and the one or more other plates, and wherein the slit portions formed at the first plate and the second plate have widths narrower than widths of the slit portions of the one or more other plates.

9. The flow path unit according to claim 1, wherein the slit portions are formed on all of the plurality of plates.

* * * * *